United States Patent
Furey (10) Patent No.: US 9,844,380 B2
(45) Date of Patent: Dec. 19, 2017

(54) ANEURYSM CLOSURE DEVICE

(71) Applicant: COOK MEDICAL TECHNOLOGIES LLC, Bloomington, IN (US)

(72) Inventor: Aidan Furey, Copenhagen (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 137 days.

(21) Appl. No.: 14/539,594

(22) Filed: Nov. 12, 2014

(65) Prior Publication Data

US 2015/0142043 A1 May 21, 2015

(30) Foreign Application Priority Data

Nov. 15, 2013 (GB) .................................. 1320178.5

(51) Int. Cl.
*A61M 29/00* (2006.01)
*A61B 17/12* (2006.01)

(52) U.S. Cl.
CPC .. *A61B 17/12113* (2013.01); *A61B 17/12036* (2013.01); *A61B 17/12109* (2013.01); *A61B 17/12159* (2013.01)

(58) Field of Classification Search
CPC ........ A61B 17/12118; A61B 17/12113; A61B 17/12145; A61B 17/12; A61B 17/12159; A61B 17/12036; A61F 2/06; A61F 2/82; A61F 2/91; A61M 29/00
See application file for complete search history.

(56) References Cited

U.S. PATENT DOCUMENTS

| | | |
|---|---|---|
| 6,309,367 B1 | 10/2001 | Bookc |
| 6,613,074 B1 | 9/2003 | Mitelberg et al. |
| 2006/0200234 A1 | 9/2006 | Hines |
| 2007/0088387 A1 | 4/2007 | Eskridge et al. |

(Continued)

FOREIGN PATENT DOCUMENTS

| | | |
|---|---|---|
| EP | 1 281 355 A2 | 7/2002 |
| EP | 2873379 | 9/2014 |

(Continued)

OTHER PUBLICATIONS

GB Examination Report for GB 1320178.5, dated Oct. 20, 2015 (2 Pages).

(Continued)

*Primary Examiner* — Victor Nguyen
(74) *Attorney, Agent, or Firm* — Brinks Gilson & Lione (57) ABSTRACT

An aneurysm closure device or flow diverter includes a frame member formed of crossing frame elements and a diverter portion formed of a plurality of blade elements extending in radially opposing directions from a diverter element. The flow diverter is ideally suited for diverting the flow of fluid from an aneurysm at a vessel bifurcation, whereupon the blade elements and diverter element can be positioned at the neck of the aneurysm so as to substantially close off the flow path into the aneurysm sac. The crossing frame elements hold the device in position at the bifurcation. The structure provides reliable deployment of the device and closure of an aneurysm.

20 Claims, 7 Drawing Sheets

(56) References Cited

U.S. PATENT DOCUMENTS

2007/0293891 A1\* 12/2007 Corcoran .......... A61B 17/0057
606/213
2009/0228029 A1   9/2009 Lee
2011/0022149 A1   1/2011 Cox et al.
2012/0172927 A1\* 7/2012 Campbell .......... A61B 17/0057
606/213
2013/0152743 A1\* 6/2013 DePue .................... H02G 1/00
81/125

FOREIGN PATENT DOCUMENTS

| FR | 2890306 A1 | 3/2007 |
| WO | WO 1999/30640 A1 | 6/1999 |
| WO | WO 1999/030640 A1 | 6/1999 |
| WO | WO 2010/085344 A1 | 7/2010 |
| WO | WO 2012/118957 A2 | 9/2012 |

OTHER PUBLICATIONS

European Extended Search Report for EP 14275215.3-1654 dated Apr. 2, 2015 (5 Pages).
European Communication for EP 14275215.3-1664, dated Sep. 1, 2017 (3 pages).

\* cited by examiner

ANEURYSM CLOSURE DEVICE

CROSS-REFERENCE TO RELATED APPLICATIONS

This application claims the benefit of priority under 35 U.S.C. §119(a) to Great Britain Patent Application No. 1318403.1, filed Jul. 17, 2013, which is incorporated by reference here in its entirety.

TECHNICAL FIELD

The present invention relates to a vascular flow diverter and in the preferred embodiment to an aneurysm closure device. The invention also provides a method of diverting fluid flow away from an aneurysm located at a vascular bifurcation.

BACKGROUND ART

Many factors contribute to the formation of saccular aneurysms, particularly neural aneurysms. One of the major contributors is wall shear stress (WSS), which in addition to hypertension leads to a reduction in the elastic tissue of the tunica media, thereby contributing to the formation of the aneurysm. The effect of wall shear stress is heightened at certain anatomical geometries such as bifurcations, for instance at the point where the basilar artery (BA) divides into the posterior cerebral arteries (PCA).

It is known to try to treat aneurysms by filling the aneurysm sac with a filler such as a prosthetic coil. The methodology behind the use of prosthetic coils is to establish a hard thrombus formation within the sac as a means of isolating the aneurysm wall from the flow of blood. While this can be effective in the treatment of many types of aneurysm, it is less effective when the aneurysm occurs at a bifurcation or trifurcation, such as at the base of the basilar artery.

It is also known to close off the entrance to the aneurysm sac or to divert the flow of fluid therefrom, but known devices are not always optimal and in general not always suitable for treatment of aneurysms at vascular bifurcations.

Examples of devices for treating aneurysms can be found in WO-2010/085344, U.S. Pat. No. 6,309,367, U.S. Pat. No. 6,613,074, US-2006/0200234, US-2007/0088387, US-2009/0228029 and US-2011/022149.

SUMMARY OF THE INVENTION

The present invention seeks to provide improved treatment of aneurysms, in particular by means of an implantable flow diverter or aneurysm closure device. The present invention also seeks to provide an improved method of diverting fluid flow away from an aneurysm located at a vascular bifurcation.

According to an aspect of the present invention, there is provided a vascular flow diverter including: a frame member having first and second ends, the frame member including a support element at the first end and a plurality of frame struts extending from the support element towards the second end; and a diverter element including a plurality of blade elements attached to and extending from a central diverter element attached to the support element of the frame member, the blade elements being resiliently deformable and having a non-biased condition in which the blade elements extend radially outwardly from the support element and away from the frame struts.

As is described in detail below, the flow diverter is designed to locate across the opening or neck of an aneurysm so as to divert flow of blood away from the aneurysm sac. The frame member is able to hold the diverter in position in a patient's vessel, in the preferred embodiment in the space at the bifurcation between the base of the basilar artery and the start of the posterior cerebral arteries. The blade elements are able to flex when the device is deployed, thereby to adopt the shape of the vessel walls and hold the device in the correct position.

The central diverter element can act to divert blood flow as well as, in the preferred embodiments, to close off or obstruct the entry into the aneurysm sac.

Preferably, the vascular flow diverter includes at least four blade elements, extending from the support element in radially spaced orientations. The specific embodiment disclosed below and shown in the drawings has eight blade elements.

The blade elements advantageously extend at regularly spaced radial intervals.

It is preferred that the blade elements curve in a direction away from the frame member when in the non-biased condition. The blade elements could be said to be, when non-biased, concave when viewed in a direction from the first end to the second end of the frame member. Such a shape enables the blade elements to follow forwardly curving vessels, such as the side vessels of a bifurcation.

In an embodiment, the blade elements are curved in a direction normal to an axis through the first and second ends of the frame member.

Preferably, the blade elements widen in a direction from the support element.

The blade elements are advantageously deformable towards the frame member. This enables the blade elements to curve backwardly so as to follow the curvature of a backwardly curving vessel wall.

Then central diverter element may be substantially circular. The diverter element and blade elements could be formed, for example, as a cutting from a common sheet of material.

In the preferred embodiment, the frame member includes first and second frame struts each having a generally annular shape and connected to one another at least at a first inter-crossing location. The first and second frame struts are outwardly expandable.

Advantageously, the first and second frame struts provide a generally spherical shape to the frame member; which optimizes their positioning within a patient's vessel, particularly at a bifurcation.

The vascular flow diverter may be made of a spring material or a shape memory material, for instance a nickel titanium alloy such as Nitinol.

Preferably, the flow diverter includes at least one radiopaque marker.

Also disclosed is a method of diverting fluid flow away from an aneurysm located at a vascular bifurcation, including the steps of: positioning a vascular flow diverter at the location of the bifurcation, the flow diverter including a frame member having first and second ends, the frame member including a support element at the first end and a plurality of frame struts extending from the support element towards the second end; and a diverter element including a plurality of blade elements attached to and extending from the support element of the frame member, the blade elements being resiliently deformable and having a non-biased condition in which the elements extend at least in radially opposing directions from the support element and away from the frame struts; and orienting the flow diverter such that the first end of the frame element and the diverter element are positioned adjacent and facing the aneurysm, wherein at least two of the blade elements of the diverter element extend into branch vessels leading from the bifurcation, and wherein the diverter element acts to divert the flow of blood away from the aneurysm.

Preferably, some of the blade elements are biased to follow the shape of a vessel wall of the branch vessels.

Other features of the apparatus and method disclosed herein will become apparent from the following specific description of preferred embodiments.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

There are described below various embodiments of apparatus for diverting flow from an aneurysm and able in the preferred embodiment to close access to the aneurysm sac. The teachings herein are particularly useful for the treatment of aneurysms occurring at a vascular bifurcation, such as the bifurcation between the basilar artery and the posterior cerebral arteries. In the case of aneurysm treatment, once pressure is removed from within the aneurysm sac the weakened wall tissue can remodel and may heal fully.

Referring first to FIGS. 1 to 4, these show in schematic form the fitting of a known flow diverter across an aneurysm formed at the bifurcation between the basilar artery 10 of a patient and the posterior cerebral arteries 12, 14. As can be seen in these Figures, the aneurysm has formed at the bifurcation of the basilar artery 10, caused by the pressure of the blood flow on the vessel wall at the point of bifurcation. The prior art treatment shown involves first placing within the aneurysm sac an embolization coil 18. Subsequently, a flow diverter device 20 is deployed within the patient's vessels, this being in the form of a multiple stent structure. More specifically, once the coil 18 has been implanted into the aneurysm sac 16, a first stent 22 is fitted between the basilar artery 10 and one of the posterior cerebral arteries 14. The stent 22 includes a fenestration 24, not visible in FIG. 1 but apparent from FIGS. 2 and 3 and partially visible in FIG. 4, which is oriented during deployment of the stent 22 so as to face the other posterior cerebral artery 12.

Figure 1:
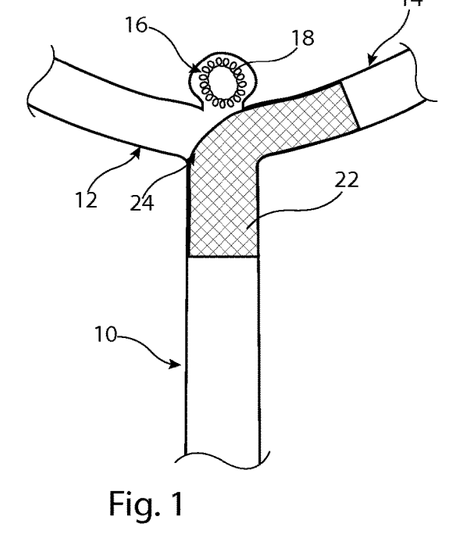
FIGS. 1 to 4 show the deployment of a conventional stent-based flow diverter device at a vascular bifurcation.
Figure 2:
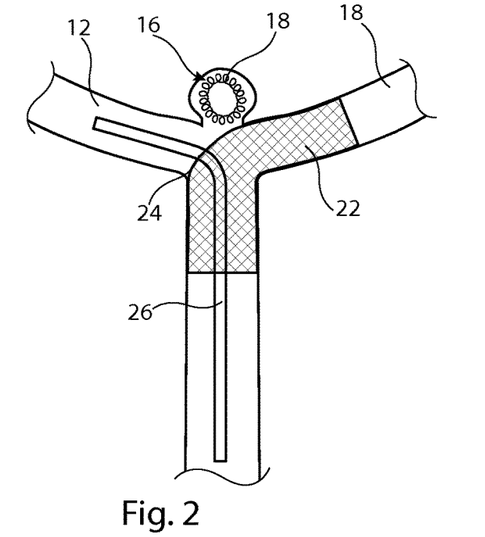
Figure 3:
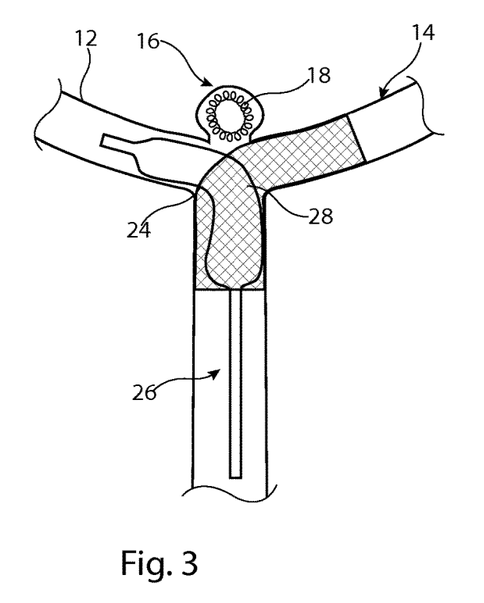
Figure 4:
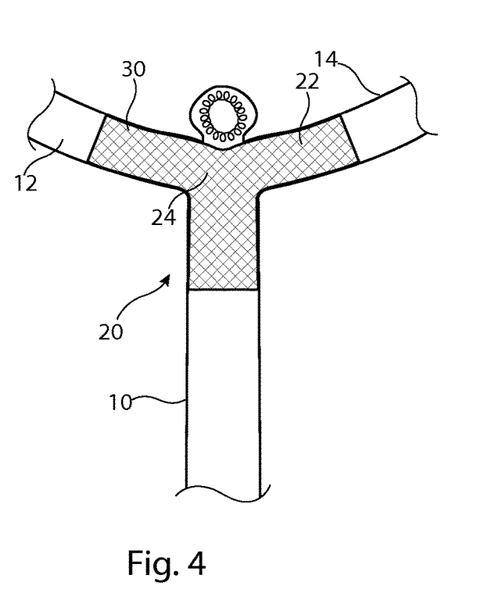

In a third stage of the deployment procedure, a deployment catheter 26 is fed through the fenestration 24 of the stent 22 such that its distal end passes into the posterior cerebral artery 12, as shown. The deployment catheter 26 includes an inflatable balloon 28 on which is mounted a second, balloon expandable, stent 30. Expansion of the balloon 28 expands the second stent 30 so that the latter becomes deployed within the posterior cerebral artery 12 and having its proximal end expanded within the proximal end of the first stent 22. Thus, as shown in FIG. 4, the double stent structure 22, 30 is fitted across the bifurcation between the basilar artery 10 and the first and second posterior cerebral arteries 12,14, thereby to isolate the aneurysm 16. The stents may have a structure of struts or wires sufficiently dense to reduce the flow of fluid into the aneurysm 16, but in other embodiments may support a covering such as graft material to create an impermeable barrier through the sides of the stents.

Whilst an assembly of the type shown in FIG. 4 can provide satisfactory isolation of an aneurysm 16, stent deployment is generally limited both in terms of access and the orientation of the anatomy at the site of the aneurysm. Stent deployment is therefore not a generic solution for all vessel anatomies. In particular, the bifurcation between the basilar artery and the posterior cerebral arteries is one such anatomy which provides a specific challenge regarding stent orientation during deployment.

FIGS. 5 to 8 show a preferred embodiment of vascular flow diverter 50. This embodiment is particularly useful for implantation at the bifurcation between the basilar artery and the posterior cerebral arteries.

Figure 5:
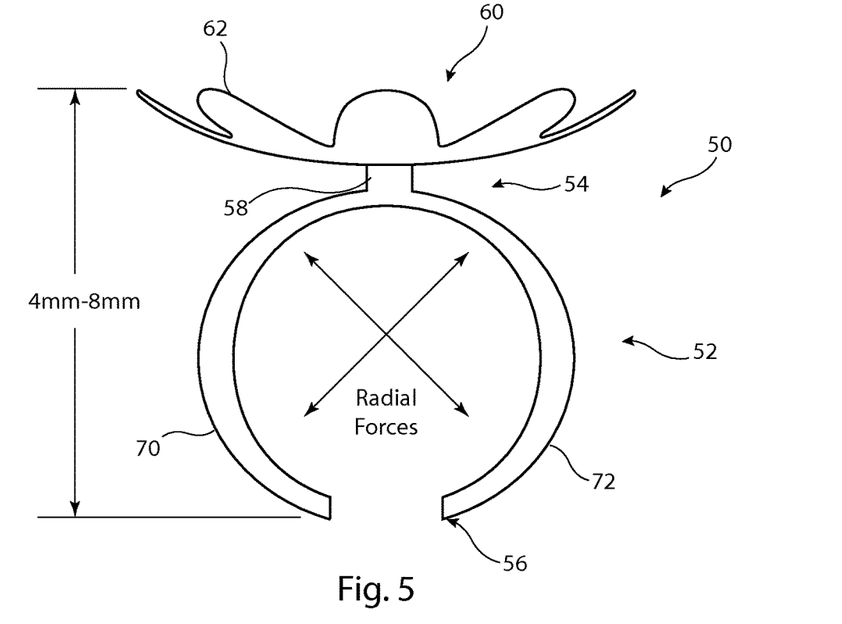
FIG. 5 is a front elevational view of a preferred embodiment of flow diverter according to the teachings herein.

Referring first to FIG. 5, the embodiment of flow diverter 50 shown includes a frame member 52 having a first end 54 and second end 56. The first end 54 is coupled to a support member 58 which in this embodiment is in the form of a curved strut fixed to annular struts of the frame member 52 (described in further detail below). Coupled to the support member 58 is a diverter element 60 which includes a plurality of blade elements 62, attached to and extending radially from the support element 58. The blade elements 62 are resiliently deformable, as described in further detail below, and have a non-biased condition, shown in FIGS. 5 to 8, in which the blade elements 62 extend in radially opposing directions from the support element 58, that is radially outwardly from a centre of the diverter element 60. The blade elements also extend in a direction away from the frame member 52. In the embodiment shown, the blade elements 62 curve away from the frame member 52 in what could be described with reference to the orientation of FIGS. 5 and 6 as at least in an upward direction towards their cantilevered extremities. In other embodiments the blade elements 62 could all lie in a common plane.

The blade elements 62 are separate from, that is unconnected to, on another along their lengths, that is only attached at the center of the diverter element 60, and are able to defect independently of one another. Thus, one blade element 62 could deflect in one direction and its neighboring elements 62 made to deflect in the opposite direction.

There are preferably provided at least four blade elements 52, in the embodiment shown there being eight in total. Any number from four to greater than eight may be used, although it is preferable that there is an even number of blade elements 62. It is also preferred that the blade elements 62 are arranged in opposing pairs. Preferably, the blade elements 62 are radially evenly spaced from one another around center point of the diverter element 60.

Figure 6:
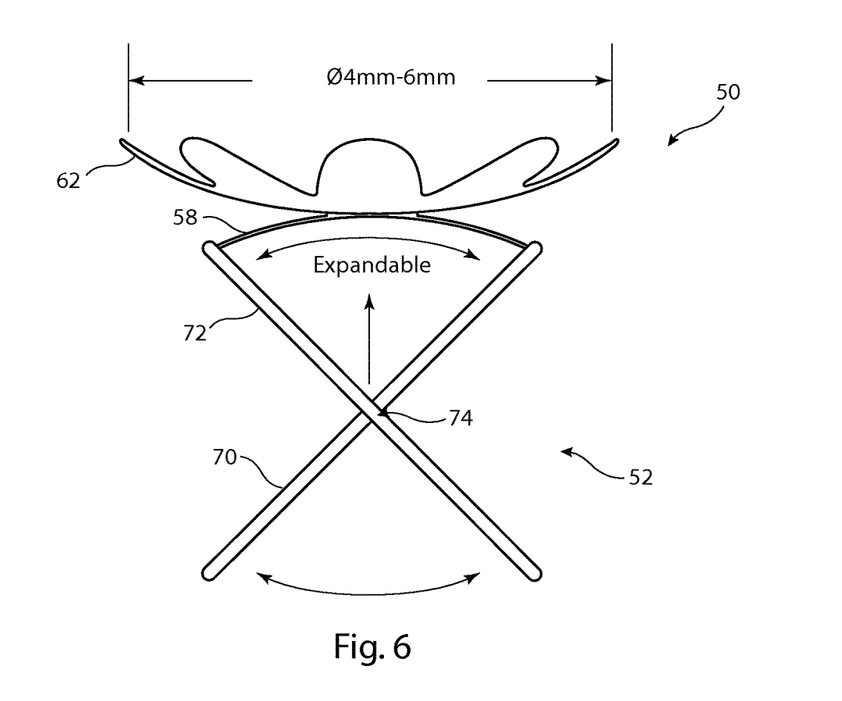
FIG. 6 is a side elevational view of the embodiment of flow diverter of FIG. 5.

Referring now to FIG. 6, the flow diverter 50 is shown in side elevation, such that the crossing frame elements 70, 72 of the frame 52 can be seen. The frame elements 70, 72 are attached to one another at a crossing point 74, of which there are two at opposite sides of the frame 52, as will be apparent in particular from FIG. 8. Each of the frame elements 70, 72 is substantially circular and in the form of a broken ring, being open at the second end 56 of the frame member 52. Open rings of this nature increase the flexibility of the device, in particular its compressibility for endoluminal delivery into a patient.

FIG. 6 also shows the arched strut forming the support element 58, fixed to a first end 54 of the crossing frame elements 70, 72. The support element is preferably in the form of a flexible flat strip of metal or metal alloy.

Figure 7:
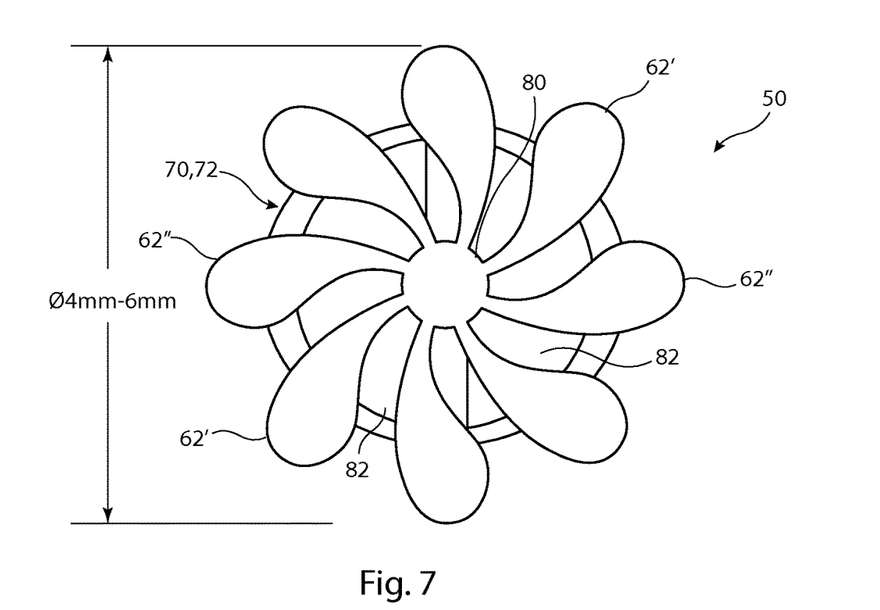
FIG. 7 is a plan view of the embodiment of flow diverter of FIG. 5.
Figure 8:
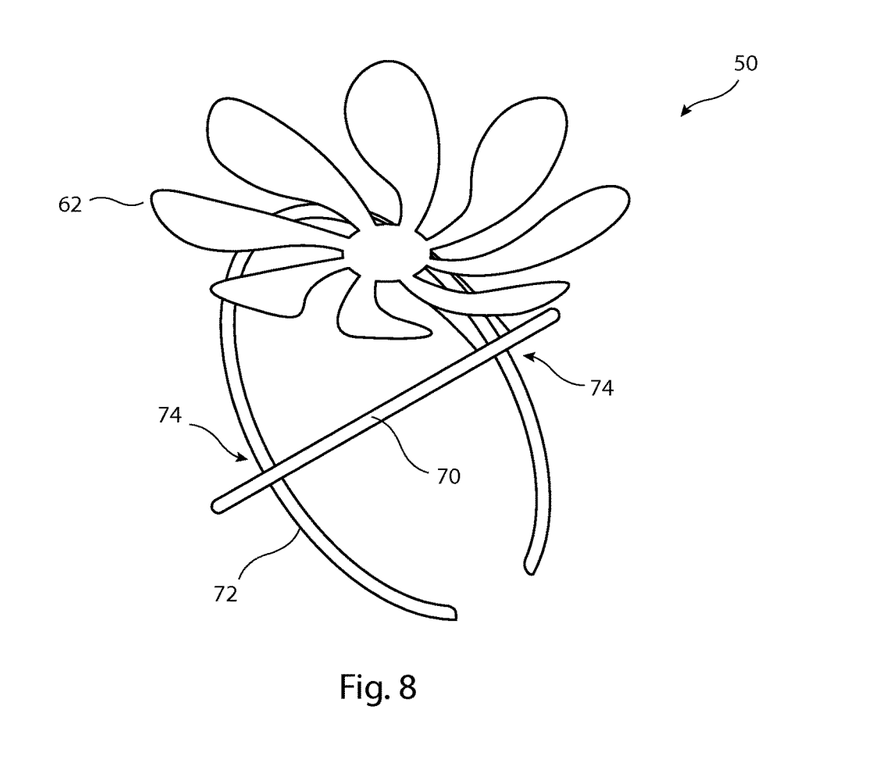
FIG. 8 is a perspective of the embodiment of flow diverter of FIG. 5.

With reference to FIG. 7, this shows the flow diverter 50 in plan view. As can be seen, in this embodiment there are provided eight blade elements arranged in opposing pairs 62'/62', 62"/62" and so on. The blade elements 62 are relatively narrow at their inner ends, at the support 58, and are relatively wider at their free extremities. Moreover, in this embodiment, blade elements 62 also curve radially from one end to another, as will be apparent in FIG. 7. This curvature enables the blade elements 62 to deflect so as to lie on top of one another in a delivery catheter. It can also assist in the placement and deployment of the flow diverter 50.

In the view of FIG. 7, and a feature of the preferred embodiments, there can be seen located at the centre point of the flow diverter 50 a flow diverter element 80, which in this embodiment is substantially circular and attached to the support element 58. The flow diverter 80 is advantageously formed as a single piece with the blade elements 62, for example as a pressing or cutting from a common sheet. The diverter element 80 may have a relatively small diameter but it is preferred that it has a diameter at least approaching the diameter of the neck of an aneurysm at which the flow diverter is to be deployed, such that the diverter element 80 completely or substantially stops the flow of blood into the aneurysm 16. In such an embodiment, the diverter element 80 acts as the aneurysm closure device. The diverter element need not be sized to cover the entirety of the neck of an aneurysm as in most instances partial closure will be sufficient to provide the required reduction in pressure in the aneurysm sac to a level to stop further deterioration of the vessel wall and to allow recovery and remodeling.

The flow diverter 50 is made of a flexible material, such as spring steel, and preferably a shape memory material such as a nickel titanium alloy, typically Nitinol. When made of a resilient material, the frame member 52 will generate radial expansion forces in the direction of the arrows shown in FIGS. 5 and 6. These forces are generated, it will be appreciated, by ensuring that the frame member 52 is oversized relative to the vessel in which the flow diverter 50 is deployed. In this particular example, the dimensions indicated in FIGS. 5, 6 and 7 are suitable for a flow diverter 50 positioned at the bifurcation between the basilar artery and the posterior cerebral arteries, that is for the anatomy shown in FIGS. 1 to 4. The generation of these radial expansion forces ensures that the frame member 52 will remain securely located in the basilar artery with the diverter element 60 positioned against the point of bifurcation and in particular against the neck of the aneurysm 16.

The shape of the blade elements 62, in widening towards their extremities, provides a gap 82 between adjacent blade elements 62 which is generally the same width along the length of the blade elements 62. The size of the gap 82 can be determined on the basis of the amount of flow restriction/ diversion which is desired and the vessel anatomy. In some embodiments, all or at least the majority of flow diversion function is provided by the blade elements 62, in which case, the flow diverter element 80 need only be of minimal size or even omitted altogether, the blade elements 62 then being be coupled directly to the support element 58.

Figure 9:
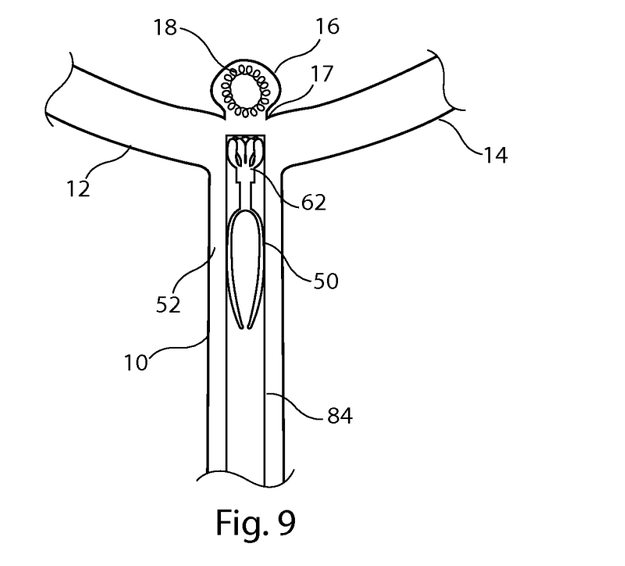
FIGS. 9 to 11 show the embodiment of flow diverter of FIGS. 5 to 8 in the course of deployment in a patient.
Figure 10:
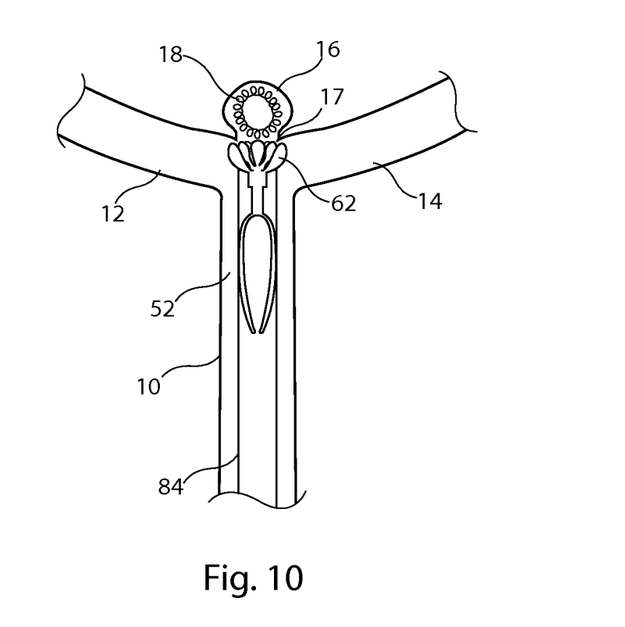
Figure 11:
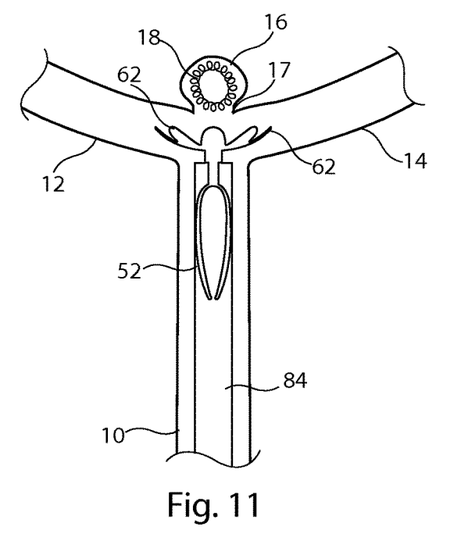

Referring now to FIGS. 9 to 11, these show an example of deployment of the flow diverter 50 of FIGS. 5 to 8 in the basilar artery 10 and in particular at the bifurcation with the posterior cerebral arteries 12, 14, so as to divert blood flow from an aneurysm 16. In the example shown in FIGS. 9 to 11, an embolization coil 18 has been implanted in the aneurysm in accordance with conventional practice, although this is not essential as the flow diverter 50 can be used singularly to close off the aneurysm 16.

In the schematic diagrams of FIGS. 9 and 10 only the catheter 84 of a delivery or introducer assembly is shown, for the sake of clarity. The skilled person will readily appreciate the type of components which will be included in the delivery or introducer assembly as these are conventional in the art. These components will typically include a pusher rod within the catheter 84, for pushing the medical device out of the distal end of the catheter, restraining wires or the like for holding the medical device in a radially constrained condition during delivery, and so on. As already stated, these are elements which will be familiar to the person skilled in the art.

Referring to FIG. 9, it can be seen that the flow diverter 50 is held in a radially constrained configuration in which the crossing frame elements 70,72 are pressed radially inwardly and the blade elements 62 are pressed in a forwards direction so as to reduce their radial reach. The elements 62,72 can be held in this position by suitable restraining wires of the introducer assembly. It is to be understood that in other embodiments the blade elements 62 can be bent backwardly, that is in a direction towards crossing frame elements 70, 72, such that the diverter element 80 would be the distal-most part of the flow diverter 50 when held within the catheter 84.

The distal end of the catheter 84 is positioned at the bifurcation between the basilar artery 10 and the posterior cerebral arteries 12,14, just slightly spaced from the neck 17 of the aneurysm 16. This enables, as will be apparent from a comparison of FIGS. 10 and 11, the deployment of the blade elements 62 while these are being pushed out of the distal end of the catheter 84, whereupon they will splay radially outwardly to spread around the neck 17 of the aneurysm 16. Once the blade elements 62, and therefore the flow diverter part of the medical device 50, have opened up and been positioned over the aneurysm 16, the remainder of the device 50 can be pushed of the catheter 84 and expanded to the vessel walls, thereby holding the device in position.

It will appreciated that when the medical device 50 is made of a shape memory material, such as Nitinol, the elements 62, 72 of the medical device 50 will not generate a significant return force until the device has exceeded the transition temperature, which will typically be set around body temperature. This will assist in holding the medical device 50 in a radially contracted configuration before deployment.

Referring now to FIGS. 12 to 16, these show in schematic form the flow diverter 50 fully deployed within the vessel at the bifurcation between the basilar artery and the posterior cerebral arteries 12,14.

Figure 12:
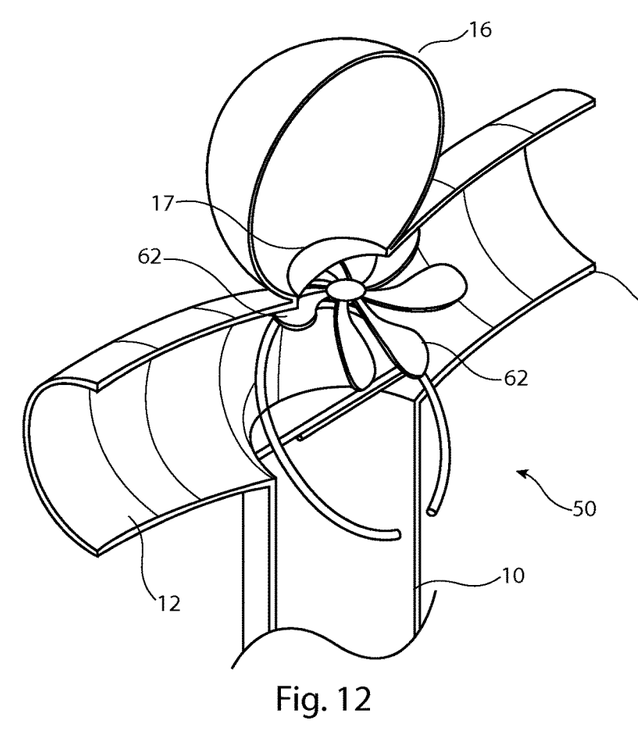
FIGS. 12 and 13 are perspective views of the flow diverter of FIGS. 5 to 8 positioned at the bifurcation.
Figure 13:
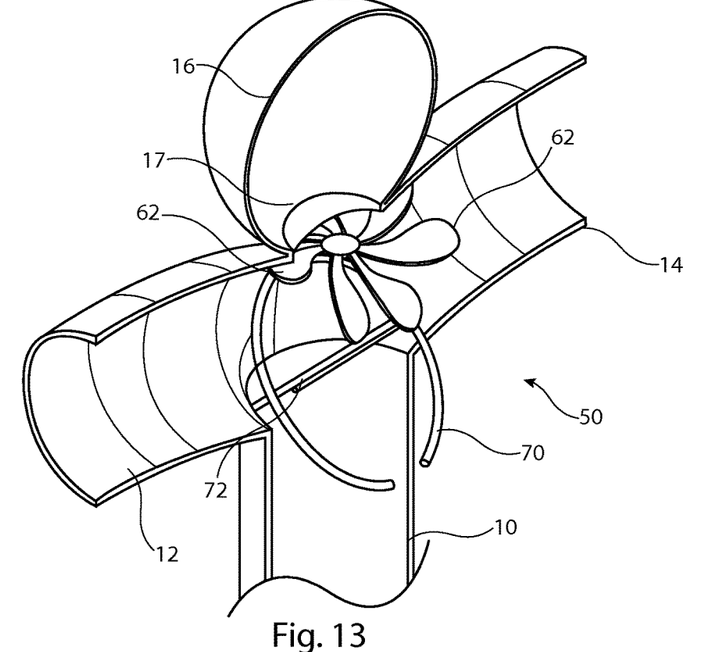

As can be seen in the perspective views of FIGS. 12 and 13, the flow diverter 50 is fully deployed at the bifurcation, with the flow diverter member 80 positioned against the neck 17 of the aneurysm 16 and the frame legs 70, 72 expanded into the junction between the basilar artery 10 and the posterior cerebral arteries 12,14. The spherical nature of the crossing frame elements 70, 72 is ideally suited to the anatomy of this bifurcation and will hold the flow diverter 50 in place while applying pressure on the diverter portion 60 towards the neck of the aneurysm 16. The flexibility and open nature of the crossing frame elements 70, 72 ensures that these can produce a constant biasing force to hold the device 50 in the correct position.

Figure 14:
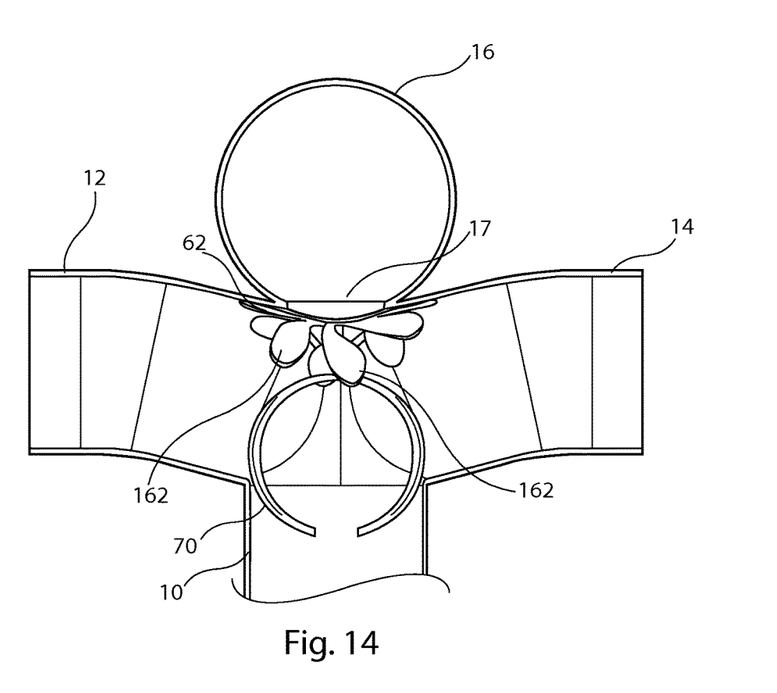
FIGS. 14 and 15 are front elevational views of the flow diverter of FIGS. 5 to 8 positioned at the bifurcation.
Figure 15:
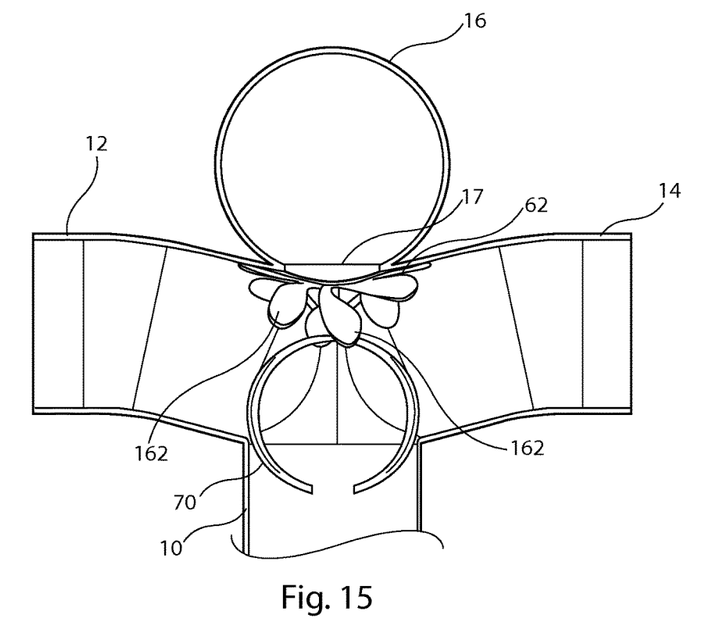
Figure 16:
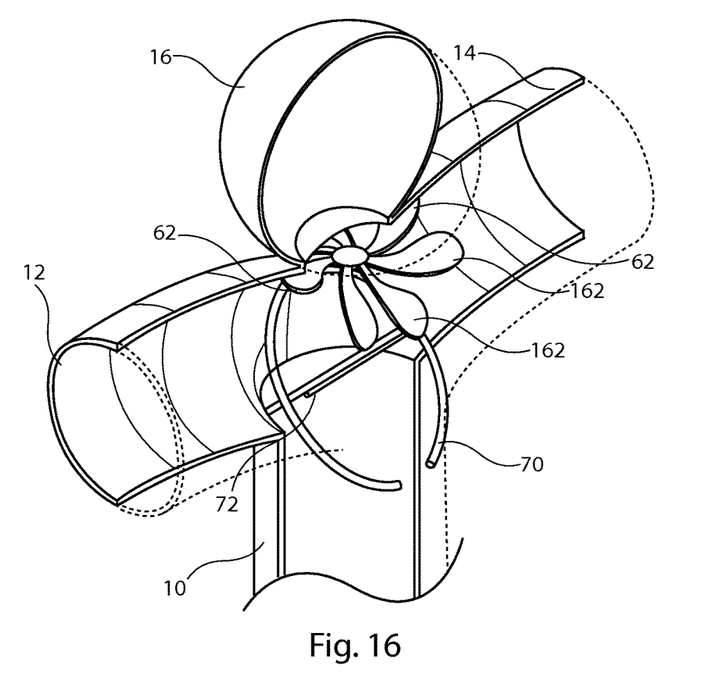
FIG. 16 is a schematic perspective view of the flow diverter of FIGS. 5 to 8 located within a patient's vessel.

With reference to FIGS. 14 to 16, the blade elements 62 will curve in dependence upon the shape of the vessel wall which they abut. Some of the frame elements 62 will remain substantially straight, thereby to lie along the vessel wall 14 adjacent to the opening 17 of the aneurysm 16, whereas other blade elements, denoted by reference numeral 162 in FIGS. 12 to 16, will curve backwardly, that is towards the frame member 52, as a result of the curvature of the vessel walls. Thus, the blade elements 62, and as a result the diverter part of the medical device 50, will take the shape of the vessels against which they are pressed. The forwardly or upwardly curving nature of the blade elements 62 explained particularly with reference to FIGS. 5 and 6 above, will ensure the blades will contact the sides of the vessels 12,14 even when these curve slightly backwardly with respect to the opening 17 to the aneurysm 16.

As well as ensuring good contact and therefore closure with the neck 17 of the aneurysm 16, the shape and nature of the blade elements 62, and in particular the independence of the blade elements, being unconnected from one another along their lengths, enables the blade elements to deflect independently of one another, to ensure that the medical device 50 will remain in the correct orientation in the vessel over time. This can make the device suitable for long term or permanent implantation in a patient.

The symmetrical arrangement of the blade elements 62 and shape of the frame element 50 allows the device to be positions in any angular orientation relative to the neck 17 of the aneurysm 16, as the each blade 62 is able to flex in any of the orientations shown. The device therefore need not be deployed in any particular rotational position, in contrast to a stent based diverter assembly of the type shown in FIGS. 1 to 4.

Although not shown in the drawings, it is preferred that the device 50 is provided with one or more radiopaque markers for use in detecting the position of the medical device. These radiopaque markers could be located, for instance, on the blade elements 62, at the diverter element 80, on the support element 58, on the crossing frame elements 70, 72, or any combination of these. It is also envisaged that in some embodiments some or all of the elements forming the device 50 could be made of materials which are or incorporate radiopaque material.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

I claim:

1. A vascular flow diverter including:
a frame member having first and second ends, the frame member including a support element at the first end and a plurality of frame struts extending from the support element towards the second end, the frame struts each being substantially circular and in a form of a broken ring open at the second end of the frame member; and
a diverter element including a plurality of blade elements attached to and extending from the support element of the frame member, the blade elements being resiliently deformable and having a non-biased condition in which the elements extend radially outwardly from the support element and away from the frame struts.

2. The vascular flow diverter according to claim 1, including at least four blade elements, said blade elements extending from the support element in radially spaced directions.

3. The vascular flow diverter according to claim 2, including at least eight blade elements.

4. The vascular flow diverter according to claim 1, wherein the blade elements extend at regularly spaced radial intervals.

5. The vascular flow diverter according to claim 1, wherein the blade elements are arranged in opposing pairs around the support element.

6. The vascular flow diverter according to claim 1, wherein the blade elements curve in a direction away from the frame member when in the non-biased condition.

7. A vascular flow diverter including:
a frame member having first and second ends, the frame member including a support element at the first end and a plurality of frame struts extending from the support element towards the second end, the frame struts each being substantially circular and in a form of a broken ring open at the second end of the frame member; and
a diverter element including a plurality of blade elements attached to and extending from the support element of the frame member, the blade elements being resiliently deformable and having a non-biased condition in which the elements extend radially outwardly from the support element and away from the frame struts;
wherein the blade elements curve in a direction away from the frame member when in the non-biased condition; and
wherein in the non-biased condition the blade elements are concave when viewed in a direction from the first end to the second end of the frame member.

8. The vascular flow diverter according to claim 1, wherein the blade elements are curved in a direction normal to an axis through the first and second ends of the frame member.

9. The vascular flow diverter according to claim 1, wherein the blade elements widen in a direction from the support element.

10. The vascular flow diverter according to claim 1, wherein the blade elements are deformable towards the frame member.

11. The vascular flow diverter according to claim 1, wherein the support element includes a central diverter element attached to the support element and from which the blade elements extend.

12. The vascular flow diverter according to claim 11, wherein the central diverter element is substantially circular.

13. The vascular flow diverter according to claim 1, wherein the frame member includes first and second frame struts having a generally annular shape and connected to one another at least at a first inter-crossing location.

14. The vascular flow diverter according to claim 13, wherein the first and second frame struts are outwardly expandable.

15. The vascular flow diverter according to claim 13, wherein the first and second frame struts provide a generally spherical shape to the frame member.

16. The vascular flow diverter according to claim 1, made of a spring material or a shape memory material.

17. The vascular flow diverter according to claim 1, made of nickel titanium alloy.

18. The vascular flow diverter according to claim 1, including at least one radiopaque marker.

19. The vascular flow diverter according to claim 1, wherein the diverter element and the blade elements are formed as a cutting from a common sheet of material.

20. The vascular flow diverter according to claim 1, wherein the blade elements are separate from one another along their lengths and non-overlapping.

* * * * *